US010960195B2

(12) United States Patent
Garcia-Menocal (10) Patent No.: US 10,960,195 B2
(45) Date of Patent: Mar. 30, 2021

(54) DEVICE FOR ASSISTING ACCESS TO A SUBCUTANEOUS PORT (71) Applicant: Sadiel E. Garcia-Menocal, Miami, FL (US)

(72) Inventor: Sadiel E. Garcia-Menocal, Miami, FL (US)

( * ) Notice: Subject to any disclaimer, the term of this patent is extended or adjusted under 35 U.S.C. 154(b) by 101 days.

(21) Appl. No.: 15/387,128

(22) Filed: Dec. 21, 2016

(65) Prior Publication Data
US 2017/0173320 A1 Jun. 22, 2017

Related U.S. Application Data (60) Provisional application No. 62/270,198, filed on Dec. 21, 2015.

(51) Int. Cl.
*A61M 39/02* (2006.01)
*A61B 42/20* (2016.01)
*A61B 17/00* (2006.01)

(52) U.S. Cl.
CPC ........ *A61M 39/02* (2013.01); *A61M 39/0208* (2013.01); *A61B 42/20* (2016.02); *A61B 2017/00438* (2013.01); *A61M 2039/0205* (2013.01); *A61M 2039/0232* (2013.01); *A61M 2039/0238* (2013.01)

(58) Field of Classification Search
CPC .............. A61M 39/02; A61M 39/02; A61M 2039/0205; A61M 2039/0232; A61M 2039/0238; A61M 16/0497; A61M 25/02; A61M 2025/024; A61M 39/0208; A61B 42/20; A61B 2017/00438
See application file for complete search history.

(56) References Cited

U.S. PATENT DOCUMENTS

| 4,337,791 | A | * | 7/1982 | Tech ................... A61M 39/286 137/556 |
| 4,586,924 | A | * | 5/1986 | Lanning ................ A61M 5/425 128/869 |
| 5,620,419 | A | * | 4/1997 | Lui ........................ A61M 5/427 604/116 |
| 5,693,041 | A | * | 12/1997 | Murphy-Chutorian ..................... A61B 18/22 606/2 |
| 2004/0260281 | A1 | * | 12/2004 | Baxter, III ............. A61B 18/14 606/41 |
| 2005/0251093 | A1 | * | 11/2005 | Abou-Kansoul ..... A61M 1/008 604/119 |

FOREIGN PATENT DOCUMENTS

WO WO 2014155075 A1 * 10/2014 ........ A61M 39/0208

* cited by examiner

*Primary Examiner* — Nilay J Shah
(74) *Attorney, Agent, or Firm* — Murtha Cullina LLP; Anthony P. Gangemi (57) ABSTRACT The device includes a manipulation mechanism for maneuvering a base into position proximate a subcutaneous port. Arms extending from the base enable the device to receive the port and substantially immobilize the port relative to the device. The manipulation mechanism also enables a user to substantially immobilize the device relative to a patient. With the subcutaneous port substantially immobilized by the device, the user has greater confidence and accuracy when inserting a needle into the port. Further, embodiments of the device provide protection to the user to prevent inadvertent sticking of the user as the needle is introduced.

13 Claims, 8 Drawing Sheets

DEVICE FOR ASSISTING ACCESS TO A SUBCUTANEOUS PORT

CROSS-REFERENCE TO RELATED APPLICATIONS

This application claims the benefit of U.S. Provisional Patent Application Ser. No. 62/270,198, filed Dec. 21, 2015, which is herein incorporated by reference in its entirety.

BACKGROUND

In the medicine and nursing arts, it is vital that each task be performed with the highest possible standards of safety and sterility in mind. One challenge faced in these fields is how to protect the users (the doctors, nurse, and the like) of medical equipment and compounds from inadvertently receiving the effects of this equipment while utilizing them to treat another individual, such as a patient. The tip of a needle does not discriminate and it is not uncommon for medical practitioners to inadvertently "stick" themselves when attempting to inject another individual.

This concern is particularly applicable when a patient or other individual has had a subcutaneous port installed. Located under the skin, the port has a septum through which drugs can be injected and blood samples can be drawn many times, usually with less discomfort for the patient than a more typical stick with a needle. A catheter then connects the port to a vein.

Figure 1:
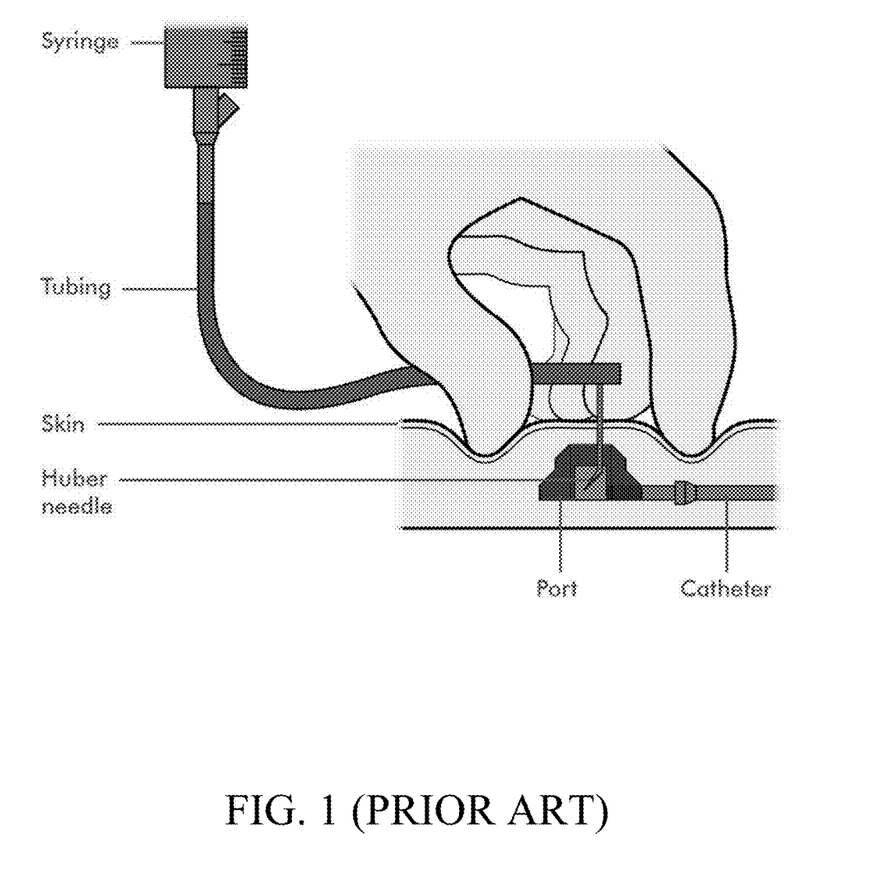
FIG. 1 portrays a prior art diagram of a technique for inserting a needle into a subcutaneous port.

FIG. 1 shows a standard catheter and port being accessed by a standard injection device using the method currently approved in the field. The port is in near constant motion due to its movement under the skin or movement of the individual in which the port is installed. Thus, the doctor or nurse's target injection site is in constant motion, leaving them even more susceptible to the dangers identified above.

To date, there are no assistive devices for accessing ports. What is desired, therefore, is the development of a device that will allow users to easily access ports while avoiding accidental needle sticks caused by patient movements, immobilize a clumsy port catheter that slides around under the skin, and ensure that the user has a clear visual field of the port's center.

SUMMARY

In some embodiments, the present disclosure is directed to a device comprising a base, a first arm, a second arm, and at least one manipulation mechanism for manipulating/maneuvering the device into position adjacent or proximate to a port in an individual receiving an injection.

The device of the present disclosure assists users in easily accessing a port without contaminating the insertion site while keeping the user (such as a nurse or doctor) and patient safe from accidental needle punctures. The device also allows the user to visualize the insertion site without having to crowd the area with fingers. The device safely secures the port while minimizing movement and allowing for correct accessing to occur the first time.

In some embodiments, the present disclosure is directed to a device for stabilizing a subcutaneous port including a base, a first arm, a second arm, and at least one manipulation mechanism. In some embodiments, the second arm opposes the first arm. In some embodiments, the first arm and the second arm extend from the base. In some embodiments, at least one of the base, the first arm, and the second arm are configured to substantially immobilize movement of a subcutaneous port with respect to the device. In some embodiments, the first arm has a first end and the second arm has a second end, wherein an opening separates the first end from the second end.

In some embodiments, the at least one manipulation mechanism is adjacent the base, the first arm, and the second arm. In some embodiments, the at least one manipulation mechanism is apart from the base, the first arm, and the second arm. In some embodiments, the at least one manipulation mechanism extends from at least one of the base, the first arm, and the second arm.

In some embodiments, the at least one manipulation mechanism is selected from the group consisting of: a handle, at least one platform, at least one tube, and combinations thereof. In some embodiments, the at least one platform is covered. In some embodiments, the at least one platform is oriented vertically. In some embodiments, the at least one platform is curved.

In some embodiments, the at least one of the base, first arm, and second arm further comprise a stabilizing mechanism. In some embodiments, the stabilizing mechanism is a sidewall. In some embodiments, the sidewall is provided at an angle.

In some embodiments, at least one of the base, the first arm, the second arm, the at least one manipulation mechanism, and the stabilizing mechanism is adjustable. In some embodiments, at least one of the base, the first arm, the second arm, the at least one manipulation mechanism, and the stabilizing mechanism is flexible.

In some embodiments, the at least one of the base, the first arm, the second arm, the at least one manipulation mechanism, and the stabilizing mechanism is configured to interface with a patient's skin and stabilize the device against the patient's skin. In some embodiments, at least one of the base, the first arm, the second arm, and the stabilizing mechanism is curved.

In some embodiments, the present disclosure is directed to a method for stabilizing a subcutaneous port including engaging via at least one manipulation mechanism a device that comprises a base, a first arm, and a second arm opposing the first arm, contacting the base with a patient proximate the subcutaneous port, thus limiting movement of the device with respect to the subcutaneous port, stabilizing the device against the patient, thus limiting movement of the device with respect to the patient's skin, and maintaining the device in a stabilized position with the base proximate the subcutaneous port until a needle is inserted into the subcutaneous port. In some embodiments, the step of maintaining the device in a stabilized position includes maintaining contact via a stabilizing mechanism between the subcutaneous port and at least one of the base, a first arm extending from the base, and a second arm extending from the base.

BRIEF DESCRIPTION OF THE DRAWINGS

The drawings show embodiments of the present disclosure for the purpose of illustrating the invention. However, it should be understood that the present application is not limited to the precise arrangements and instrumentalities shown in the drawings, wherein.

DESCRIPTION

Figure 2:
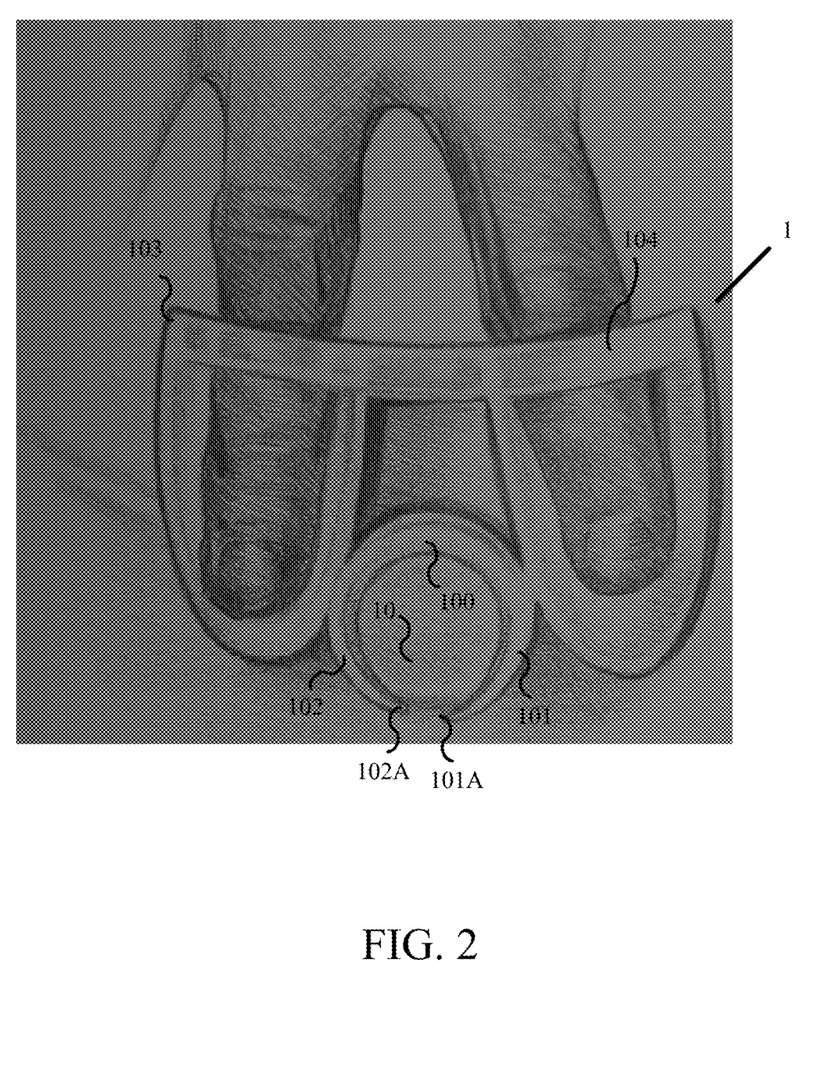
FIG. 2 portrays a device for assisting access to a subcutaneous port consistent with some embodiments of the present disclosure.
Figure 4:
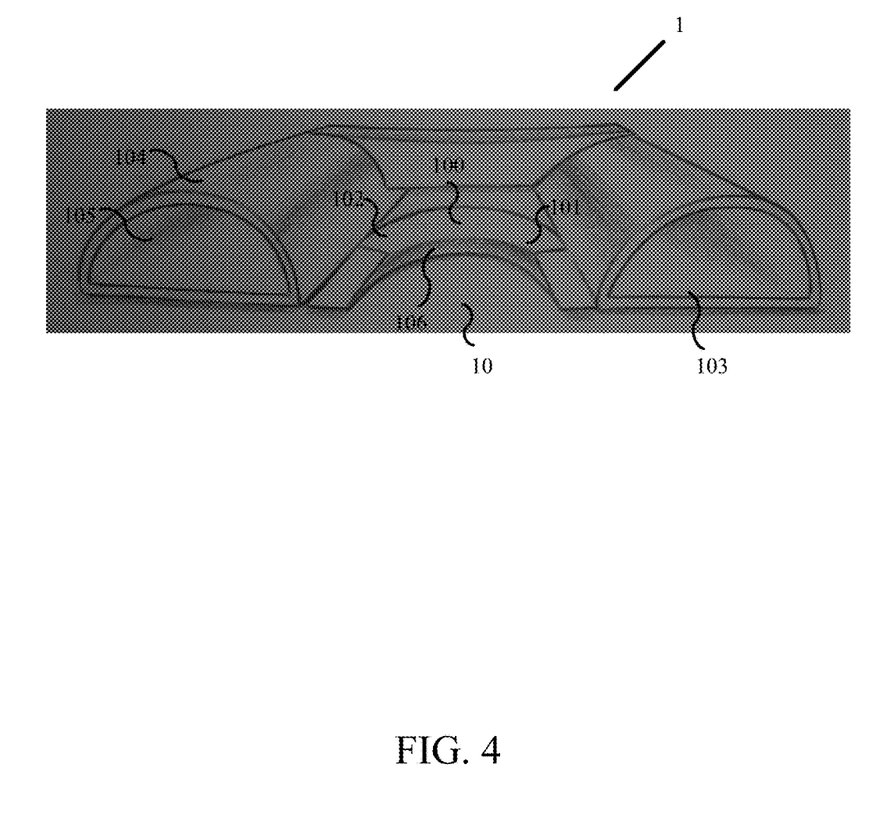
FIG. 4 portrays a further embodiment of the device shown in FIG. 2.
Figure 5:
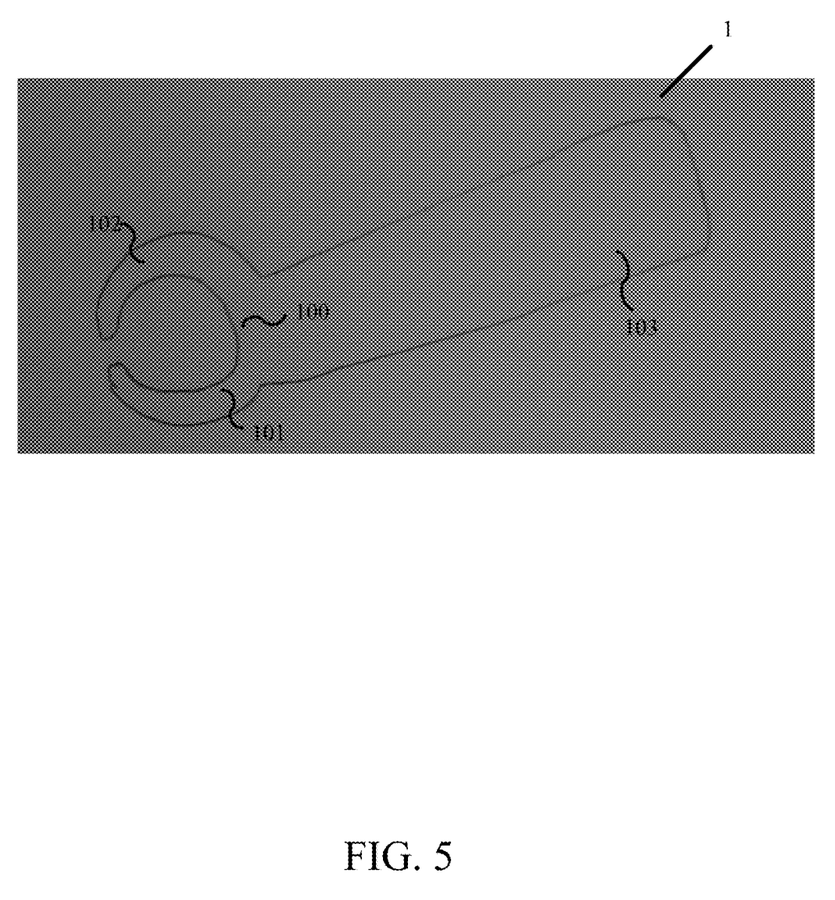
FIG. 5 portrays a further embodiment of the device shown in FIG. 2.

Referring to FIGS. 2, 4, and 5, in some embodiments, the present disclosure is directed to a device 1 for assisting a user at an insertion site 10 for an individual. In some embodiments, device 1 comprises a base 100, a first arm 101, and a second arm 102. In some embodiments, second arm 102 opposes first arm 101. In some embodiments, device 1 comprises at least one manipulation mechanism 103. In some embodiments, at least one of base 100, first arm 101, and second arm 102 are configured to substantially immobilize movement of a subcutaneous port with respect to device 1.

In some embodiments, first arm 101 has a first end 101A and second arm 102 has a second end 102A. In some embodiments, first end 101A and second end 102A are connected. In some embodiments, first end 101A and second end 102A are not connected, leaving an opening in between them through which a port may be inserted and removed from the device (as will be discussed below).

In some embodiments, first arm 101 and second arm 102 extend from base 100. In some embodiments, first and second arms are attached to the device independent of the base 100. In these embodiments, base 100 is itself attached to a single base along with separately attached first arm 101 and second arm 102. In some embodiments, base 100 is designed to brace the device against a port within an individual. When base 100 interfaces with the port, frictional forces prevent device 1 from sliding past the port. The first arm 101 and the second arm 102 then provide additional structures upon which device 1 can interface with the subcutaneous port. With base 100 substantially preventing forward movement of device 1 with respect to the port and the user, first and second arms substantially prevent side-to-side movement of device 1. In some embodiments, additional frictional forces are provided between device 1 and the patient's skin to limit movement of device 1 relative to the skin, such as through contact between manipulation mechanism platforms (discussed in greater detail below) and the skin's surface. In some embodiments, the shapes of base 100, first arm 101, and/or second arm 102 are substantially crescent-shaped. In other embodiments, the shapes of base 100, first arm 101, and/or second arm 102 are triangular, rectangular, and the like.

Figure 3:
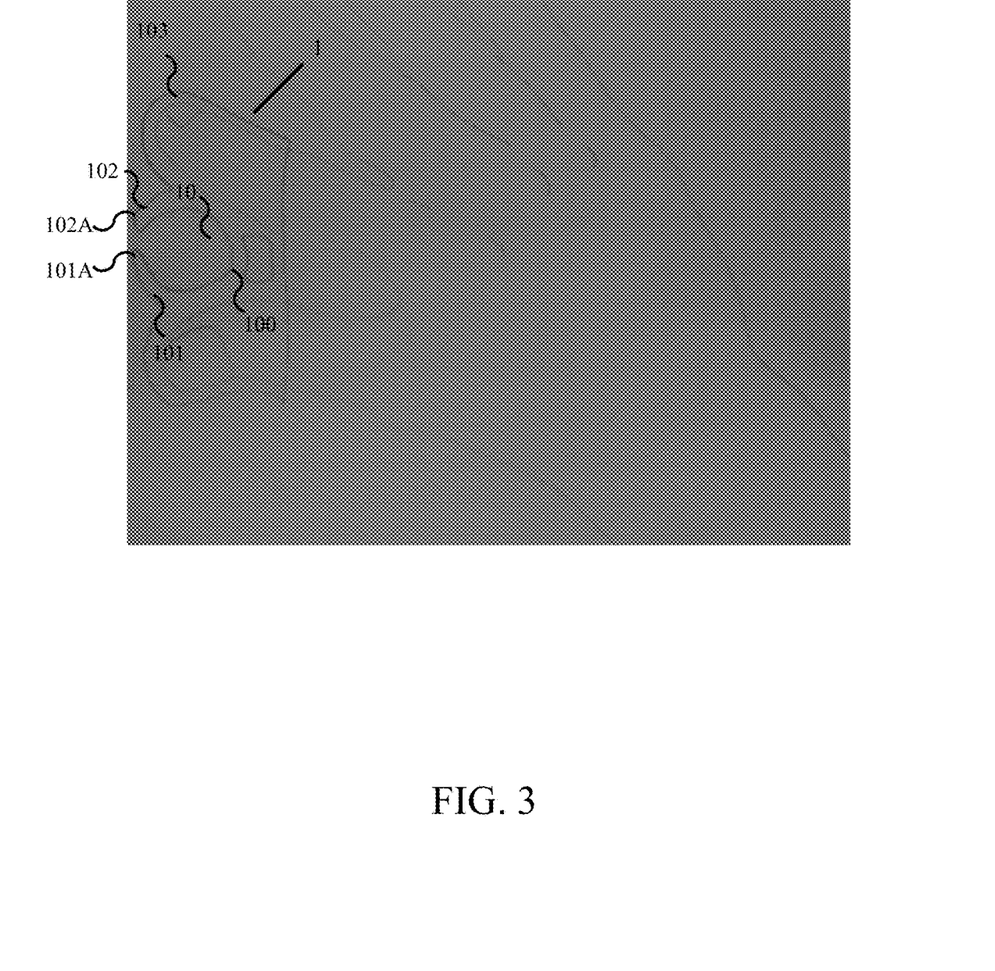
FIG. 3 portrays a further embodiment of the device shown in FIG. 2.

In some embodiments, the user engages with device 1 using their hands. In some embodiments, the user engages with device 1 using their fingers. Specific engagement schemes depend on the specific configuration of device 1 and vary based on user preference. FIG. 2 shows exemplary embodiments of the device designed to be maneuvered by a user's index and middle finger. FIG. 3 shows an exemplary embodiment of the device designed to be maneuvered by a user's index finger and thumb. One of skill in the art would understand that various combinations of a user's fingers may be used to manipulate the devices and could design platforms optimized for use with those specific finger combinations. Referring to FIG. 5, the user engages with an embodiment of device 1 at a handle via any suitable manner, such as with their palm or finger tips.

Referring again to FIGS. 2, 3, and 5, these drawings show exemplary embodiments of the above-identified manipulating mechanism 103. In some embodiments, manipulation mechanism 103 is apart from at least one of base 100, first arm 101, and second arm 102. In some embodiments, manipulation mechanism 103 is adjacent to at least one of base 100, first arm 101, and second arm 102. In some embodiments, manipulation mechanism 103 extends from base 100, first arm 101, and second arm 102. In some embodiments, manipulation mechanism 103 is at least one of a handle, at least one platform, at least one tube, and combinations thereof. In some embodiments, manipulation mechanism 103 has a covering (as will be discussed in greater detail below).

The purpose of manipulating mechanism 103 is two-fold. Firstly, manipulating mechanism 103 allows a user to position the base 100, first arm 101, and second arm 102 relative to the port. Secondly, manipulating mechanism 103 allows this positioning to occur while the user remains protected from injection devices that may be around injection site 10. One embodiment wherein manipulating mechanism 103 is shown to be a handle is shown in FIG. 5. A user grasping one end of the handle (for example, such as in the manner of a magnifying glass) is able to maneuver base 100, first arm 101, and second arm 102 at the other end of the handle. Once the port has been essentially immobilized by the user's placement of base 100, first arm 101, and second arm 102 adjacent to the port, the user can continue to hold the port in place relative to device 1 from a distance while performing other tasks, such as obtaining the relevant injection device, moving the relevant injection device into place to inject the target individual, and physically injecting the target individual using the injection device. Throughout those process steps, the user's hands and other parts of their body are protected from accidental self-injection by the distance afforded to them by the handle of device 1, thus limiting the possibility of an accident.

One embodiment wherein manipulating mechanism 103 is a plurality of platforms is shown in FIGS. 2 and 3. Referring specifically to FIG. 2, the platforms are attached to the device to provide stable regions from which a user may interact with device 1. In some embodiments, the platforms are attached to base 100. In some embodiments, the platforms are attached to at least one of first arm 101 and second arm 102. In some embodiments, interaction by objects with these platforms allows for device 1 to be maneuvered with respect to a subcutaneous port and then held in place once device 1 is moved into the proper position. Once at least one of base 100, first arm 101, and second arm 102 are moved into position adjacent to a port, the user presses on the platforms, thus pressing the device onto the skin of the individual to receive the injection. Frictional forces prevent significant movement of the device relative to the skin, and the dual platforms provide additional control to the user to prevent rotation or translation of device 1.

In some embodiments, the platforms have raised sidewalls to help position objects, such as a user's fingers, in the proper position upon the platforms. In some embodiments, the platforms are curved. In some embodiments, the platforms are oriented vertically.

Referring now to FIG. 4, in some embodiments, the platforms include at least one upper portion 104. In some embodiments, upper portion 104 covers the platform and defines a cavity 105 between it and the platform below it. In some embodiments, manipulation mechanism 103 is a tube (such as a cylindrical tube, square tube, and the like). In this embodiment, upper portion 104 acts as a shield to prevent injection devices from entering cavity 105. Upper portion 104 also provides increased surface area for enabling increased control over device 1 by a user (e.g. the covering makes it more difficult for device 1 to accidentally disengage from a user). In embodiments where device 1 is manipulated via a user's fingers inserted into these cavities 105, those fingers are shielded from the environment while the user performs other tasks such as obtaining the relevant injection device, moving the relevant injection device into place to inject the target individual, and physically injecting the target individual using the injection device. While conventional methods of injection into a subcutaneous port required the fingers of the person injecting to be close to the injection site, and thus vulnerable to errant needle sticks, upper portion 104 according to some embodiments of the instant disclosure provides protection against these sticks, as upper portion 104 would absorb the impact of the needle before it could make contact with the user's fingers.

Manipulating mechanisms 103 as described herein may be combined or multiplied as a matter of design choice that is well within the abilities of one having skill in the art.

Referring again to FIG. 4, in some embodiments, at least one of base 100, first arm 101, and second arm 102 further comprise a stabilizing mechanism 106. In some embodiments, stabilizing mechanism 106 is a sidewall. In some embodiments, stabilizing mechanism 106 is angled. In these embodiments, at least one of base 100, first arm 101, and second arm 102 have a sidewall that while normally vertical (i.e. substantially perpendicular to the skin of the individual requiring an injection) is instead angled to facilitate acceptance of the port into base 100, first arm 101, and/or second arm 102.

Figure 6:
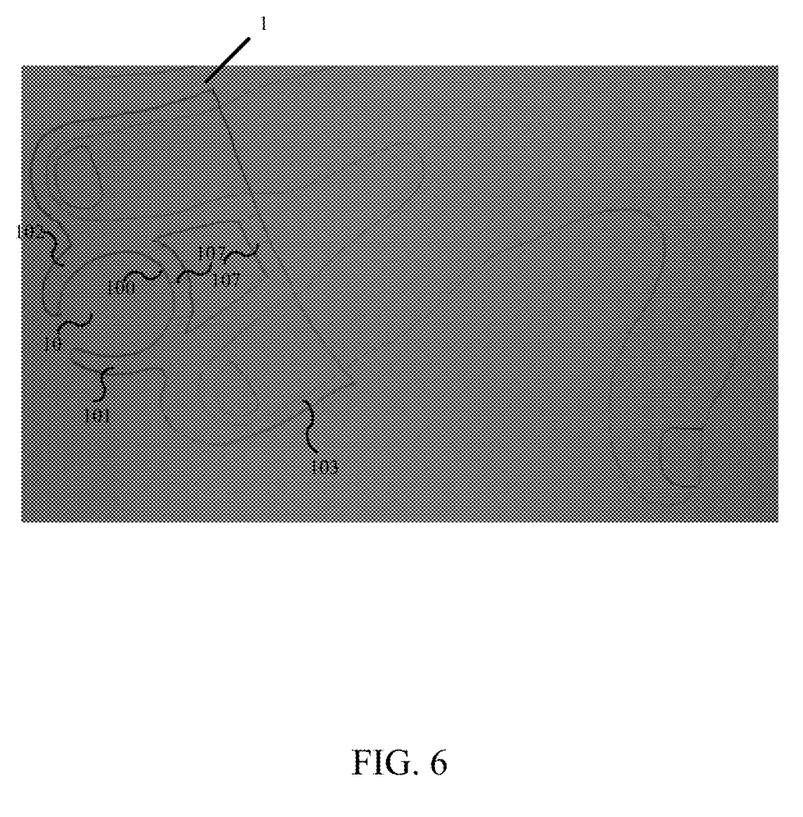
FIG. 6 portrays a further embodiment of the device shown in FIG. 2.

Referring now to FIG. 6, the embodiment shown is consistent with the embodiments described above, but further including an adjustable region 107 in base 100. In some embodiments, at least one of base 100, first arm 101, and second arm 102 are adjustable. In some embodiments, the adjustment at least one of base 100, first arm 101, and second arm 102 performed via a hinge, a ratchet, a piston, a track, and the like. By allowing the stabilizing base, the first arm, and/or the second arm to be adjustable, device 1 is more compatible with different sized ports and allows a user to have greater control over the device while in use. In the embodiment shown in FIG. 6, adjustable region 107 is a hinge placed in base 100, allowing flex at three places. With the user's fingers inserted into manipulating mechanism 103 (platforms in this case), the user can spread his or her fingers wide to open the first and second arms to the greatest possible extent (region 107 lies flat) while maneuvering device 1 towards a port. Once device 1 has been positioned, the user moves their fingers closer together, bending the hinge, and bringing first arm 101 and second arm 102 closer together. The result is a pincer movement that allows the user to more easily secure the port within device 1. The adjustability of device 1 described in this embodiment means that the above-identified method may be performed on ports of different sizes.

Figure 7:
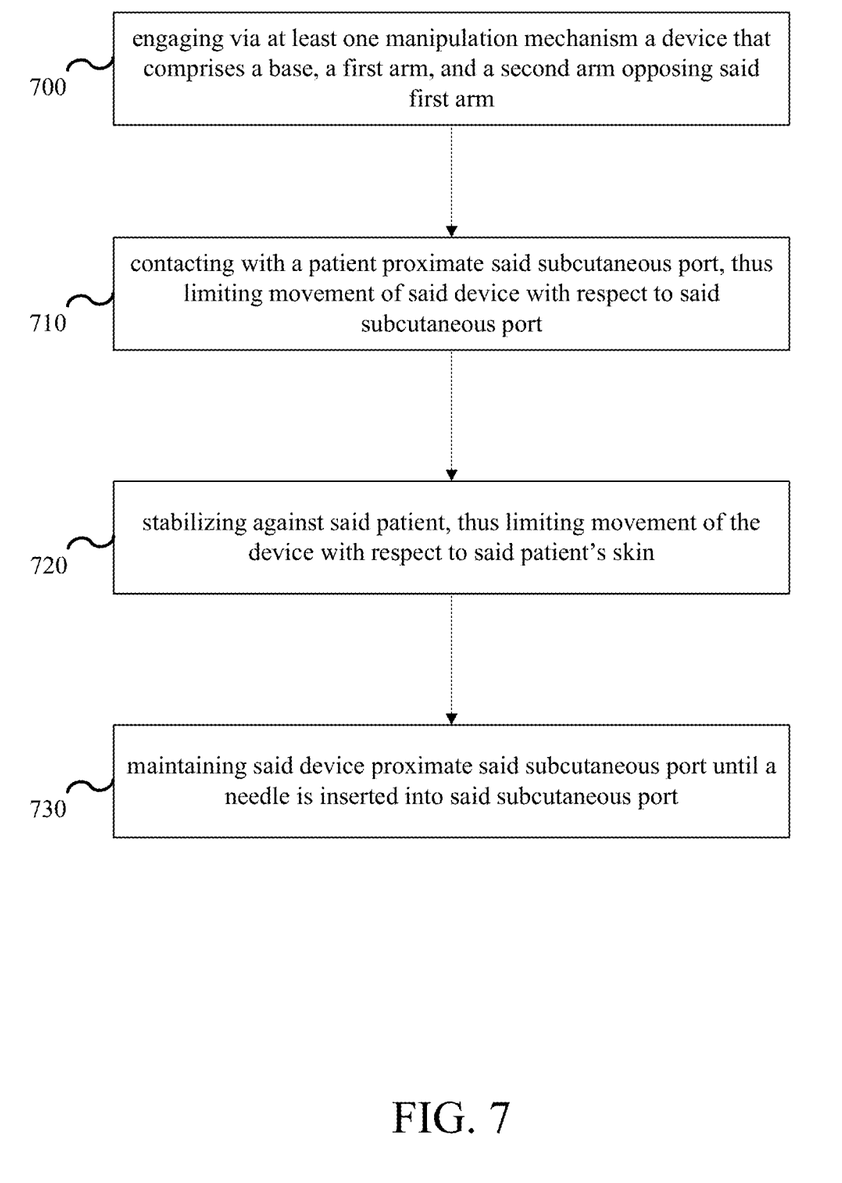
FIG. 7 portrays a method for stabilizing a subcutaneous port utilizing the device shown in FIG. 2.
Figure 8:
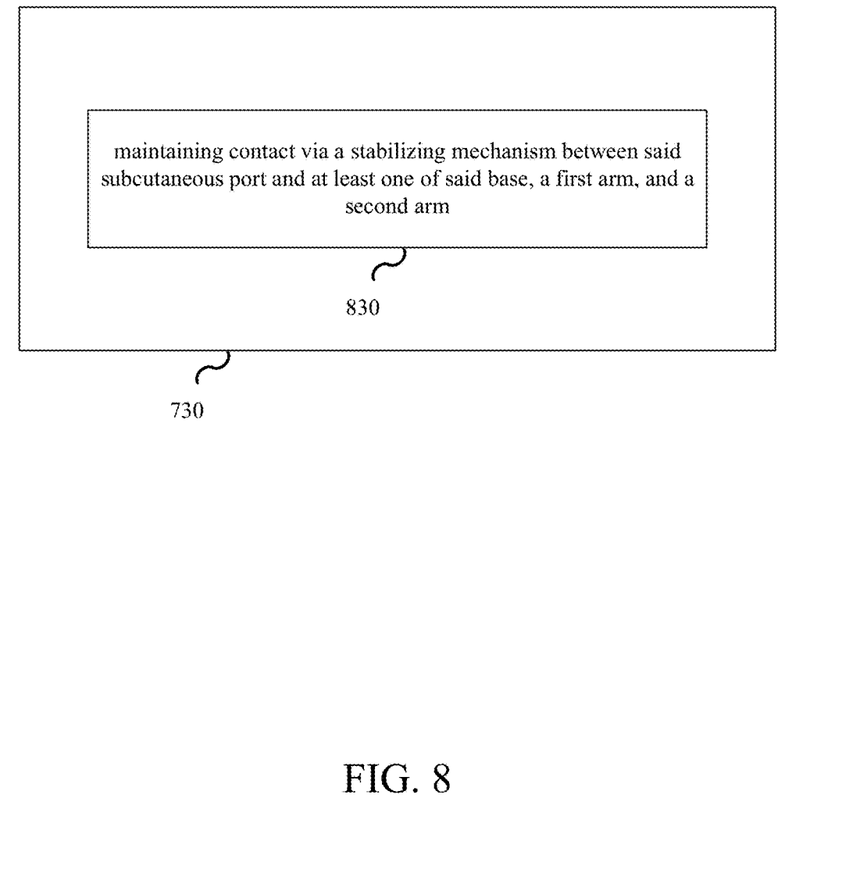
FIG. 8 portrays a further embodiment of the method shown in FIG. 7.

FIGS. 7 and 8 are directed to a method of stabilizing a subcutaneous port consistent with some embodiments of the present disclosure. In some embodiments, the method comprises the step of a user engaging 700 a device (such as device 1 described above) via at least one manipulation mechanism. The device is then contacted 710 with the patient and/or the port proximate the port and stabilized 720 there, thus limiting movement of the device relative to the port and the patient. The device contact is maintained 730 proximate the port until a needle is inserted into the port. In some embodiments, contact is maintained 830 via a stabilizing mechanism between the port and at least one of the base, firm arm, and second arm. As used herein, "contact" between a component of the device and the subcutaneous port includes "indirect" contact, i.e. where layers such as bandages, protective films, or a patient's own skin, fat, or other tissue, and combinations thereof and the like are disposed between the device and the port.

In one embodiment showing an exemplary method including a device consistent with the instant disclosure, a user identifies a subcutaneous port in an individual that is to receive an injection. The user then maneuvers the device towards the port using the manipulation mechanism. The device is then pressed onto the skin of the individual and held adjacent to the port using at least one of the stabilizing base, the first arm, and the second arm. In some embodiments, the device is held adjacent to the port with the port substantially encircled by the stabilizing base, the first arm, and the second arm. One further advantage of this embodiment is that the device itself highlights the injection site for the user, creating a clearly defined and substantially immobile target at which the user can aim the injection device. Contact between at least one of the stabilizing base, the first arm, and the second arm holds the port substantially immobile with respect to the subcutaneous port. Thus immobilized, the user injects the individual through the port. The user then removes the injection device and the device itself.

In some embodiments, while the manipulation mechanism may be directly or indirectly connected to the one or more of the stabilizing base, first arm, and second arm, the manipulation mechanism is configured such that the user interacts with the manipulation mechanism at a location remote or apart from the stabilizing base, first arm, or second arm. Configured thusly, the user manipulates the base, first arm, or second arm without the need to interact directly with any of those features using their hands or other part of their body.

The method steps discussed above may be performed in any suitable order.

In some embodiments, the device is fashioned from plastic, metal, wood, or any other suitable material and combinations thereof. In some embodiments, the device is provided as a kit having different sized devices to accommodate differently sized individuals and ports.

Although the invention has been described and illustrated with respect to exemplary embodiments thereof, it should be understood by those skilled in the art that the foregoing and various other changes, omissions and additions may be made therein and thereto, without parting from the spirit and scope of the present invention.

What is claimed is:
1. A device for stabilizing a subcutaneous port, comprising:
    a base;
    a first arm;
    a second arm opposing said first arm;
    at least one manipulation mechanism including a first platform and a second platform, wherein the first platform and the second platform are laterally adjacent the said base, said first arm, and said second arm;
    wherein said first arm and said second arm extend from said base;

wherein at least one of said base, said first arm, and said second arm are configured to substantially immobilize movement of the subcutaneous port with respect to said device, wherein said first platform is covered by a first shield to define a first cavity and said second platform is covered by a second shield to define a second cavity, said first shield configured to prevent injection devices from entering said first cavity and said second shield configured to prevent the injection devices from entering said second cavity, wherein the first shield includes a continuous outer surface extending from a first end integrated with the first platform to a second end integrated with the first platform, and the second shield includes a continuous outer surface extending from a third end integrated with the second platform to a fourth end integrated with the second platform.

2. The device according to claim 1, wherein said at least one manipulation mechanism is apart from said base, said first arm, and said second arm.

3. The device according to claim 1, wherein said at least one manipulation mechanism extends from at least one of said base, said first arm, and said second arm.

4. The device according to claim 1, wherein at least one of said base, said first arm, and said second arm further comprise a stabilizing mechanism.

5. The device according to claim 4, wherein said stabilizing mechanism is a sidewall.

6. The device according to claim 5, wherein said sidewall is provided at an angle.

7. The device according to claim 4, wherein at least one of said base, said first arm, said second arm, said at least one manipulation mechanism, and said stabilizing mechanism is adjustable.

8. The device according to claim 4, wherein at least one of said base, said first arm, said second arm, said at least one manipulation mechanism, and said stabilizing mechanism is flexible.

9. The device according to claim 4, wherein at least one of said base, said first arm, said second arm, said at least one manipulation mechanism, and said stabilizing mechanism is configured to interface with a patient's skin and stabilize the device against said patient's skin.

10. The device according to claim 4, wherein at least one of said base, said first arm, said second arm, and said stabilizing mechanism is curved.

11. The device according to claim 1, wherein said at least one of said first platform and said second platform is curved.

12. The device according to claim 1, wherein said first arm has a first arm end and said second arm has a second arm end, wherein an opening separates said first arm end from said second arm end.

13. A device for stabilizing a subcutaneous port, comprising:
- a stabilizing base;
- a first arm, said first arm having a first arm end;
- a second arm opposing said first arm, said second arm having a second arm end;
- at least one manipulation mechanism including a first platform and a second platform, wherein the first platform and the second platform are laterally adjacent the said base, said first arm, and said second arm; and
- an adjustable region including a hinge disposed between said first platform and said second platform;

wherein said first arm and said second arm extend from said base and an opening separates said first arm end from said second arm end;

wherein at least one of said base, said first arm, and said second arm comprise a stabilizing sidewall configured to maintain contact between said subcutaneous port and said device;

wherein said first platform is covered by a first shield to define a first cavity and said second platform is covered by a second shield to define a second cavity, said first shield configured to prevent injection devices from entering said first cavity and said second shield configured to prevent the injection devices from entering said second cavity;

wherein the first shield includes a continuous outer surface extending from a first end integrated with the first platform to a second end integrated with the first platform, and the second shield includes a continuous outer surface extending from a third end integrated with the second platform to a fourth end integrated with the second platform, and wherein the hinge is configured to reversibly expand the adjustable region from an elongated open configuration to a collapsed closed configuration.

* * * * *